US005637085A

United States Patent [19]
Cardinale

[11] Patent Number: 5,637,085
[45] Date of Patent: Jun. 10, 1997

[54] METHOD OF CANCER TUMOR TREATMENT BY SLOW RELEASE DELIVERY OF 1,2,4-BENZOTRIAZINE OXIDES TO TUMOR SITE

[76] Inventor: Robert M. Cardinale, 11829 Chase Wellesley Dr., #621, Richmond, Va. 23233

[21] Appl. No.: 560,856

[22] Filed: Nov. 20, 1995

[51] Int. Cl.$^6$ .............................. A61M 31/00; A61N 1/30; A61F 2/00
[52] U.S. Cl. .................. 604/49; 424/426; 604/20
[58] Field of Search .................. 424/426; 604/20, 604/49

[56] References Cited

U.S. PATENT DOCUMENTS

| | | | |
|---|---|---|---|
| 3,620,990 | 11/1971 | Hazen et al. | 521/88 |
| 4,558,690 | 12/1985 | Joyce | 604/20 |
| 4,764,364 | 8/1988 | Heller et al. | 424/426 |
| 4,978,332 | 12/1990 | Luck et al. | 604/19 |
| 5,304,377 | 4/1994 | Yamada et al. | 424/426 |

*Primary Examiner*—Peter F. Kulkosky
*Attorney, Agent, or Firm*—William J. Davis; Paul E. Dupont; Imre Balogh

[57] ABSTRACT

Disclosed are a method and composition for intralesional therapy of solid cancer tumors, and especially brain tumors, comprising, delivering a compound of a 1,2,4-benzotriazine oxide contained in a biodegradable, slow release polymer and subjecting the cancer tumors to irradiation therapy.

20 Claims, No Drawings

METHOD OF CANCER TUMOR TREATMENT BY SLOW RELEASE DELIVERY OF 1,2,4-BENZOTRIAZINE OXIDES TO TUMOR SITE

BACKGROUND OF THE INVENTION

1. Field of the Invention

The present invention relates to the field of treatments for cancer tumors. More particularly, the present invention relates to interstitial therapy for brain tumors by delivering a compound of the 1,2,4-benzotriazine oxides family contained in a biodegradable polymer slowly released to the site of the tumor.

2. Reported Developments

Glioblastoma multiforme (GBM) patient management remains a formidable task. Radiation therapy improves median survival, and the addition of chemotherapy with nitrosources adds a modest gain for selected patients (See, for example: Kornblith, P. L. et al, Chemotherapy for malignant gliomas. J. Neurosurg. 68: 1–17 (1988); and Walker, M. D. et al, Randomized comparisons of radiotherapy and nitrosoureas for the treatment of malignant glioma after surgery, N. Eng. J. Med., 303: 1323–1329 (1980)). The benefit of radiotherapy, however, is limited by several factors. Although intrinsic radioresistance and rapid cellular proliferation may contribute to therapeutic inefficacy, dose escalation has not yet yielded superior results and is limited by the radiation tolerance of normal brain as reported by Solazar, O. M. et at, High dose radiation therapy in the treatment of malignant gliomas: final report, Int. J. Radial. Oncol. Biol. Phys., 3: 1733–1740 (1979). Hypoxic radioresistance has been demonstrated in several tumor types, including GBM, and oxygen measurements document regional hypoxia in a high percentage of patients with GBM, as reported by, inter alia: Gatenby, R. A. et al, Oxygen distribution in squamous cell carcinoma metastases and its relationship to outcome of radiation therapy. Int. J. Radial. Oncol. Biol. Phys. 14: 831–838; (1988); Kayama, T. et al, Intratumoral oxygen pressure in malignant brain tumors, J. Neurosurg., 74: 55–59 (1991); Rampling, R. et al, Direct measurement of pO2 distribution and bioreductive enzymes in human malignant brain tumors, Int. J. Radiat. Oncol. Biol. Phys. 29: 427–431 (1994); and Valk, P. E. et at, Hypoxia in human gliomas: demonstration by PET with fluorine-18-fluoromisonidazole, J. Nucl. Med. 33: 2133–2137 (1992)). A treatment that kills radioresistant hypoxic tumor cells should improve the efficacy of radiation therapy.

When given as multiple injections in conjunction with fractionated irradiation, tirapazamine (SR-4233), a bioreductive agent that preferentially kills hypoxic dells, increases tumor cell kill while sparing normal tissue in mouse SCCVII and other tumors as reported by: Brown, J. M. et al, Potentiation by the hypoxic cytotoxin SR 4233 of cell killing produced by fractionated irradiation of mouse tumors, Cancer Res. 50: 7745–7749 (1990) and Brown, J. M. et al, SR 4233: a tumor specific radiosensitizer active in fractionated radiation regimens, Radiother. and Oncol., 20: 151–156 (1991). Brown has considered that tumor hypoxia may actually be of a therapeutic advantage when combining a hypoxic cytotoxin such as tirapazamine with fractionareal irradiation: Brown, J. M. et al, Tumor hypoxia: the picture has changed in the 1990s., Int. J. Radiat. Biol., 65: 95–102 (1994); and Brown, J. M. et al, Therapeutic advantage of hypoxic cells in tumors: a theoretical study, J. Nat. Can. Inst., 83: 178–185 (1991).

We have now discovered that 1, 2, 4-benzotriazine oxides contained in synthetic biodegradable polymer such as polyanhydride polymer, which allows sustained, controlled release, may be used to maximize exposure directly to the cancer tumors and target local hypoxic regions while avoiding systemic toxicity. The 1, 2, 4-benzotriazine compounds contained in said polymer is delivered to the site of the tumor by surgical implantation.

Implants made of biodegradable polymers to deliver drugs to the brain have been reported in the art, for example: Brem, H., Polymers to treat brain tumors, Biomaterials, 11: 699–710 (1990); Brem, H. et al, Biodegradable polymers for controlled delivery of chemotherapy with and without radiation therapy in the monkey brain, J. Neurosurg., 80: 283–290 (1994); and Tamargo, R. J. et at, Interstitial chemotherapy of the 9L gliosarcoma: controlled release polymers for drug delivery in the brain, Cancer Res. 53: 329–333 (1993).

None of these or other references that we are aware of pertain to a method of treating cancer tumors by implantation of a biodegradable polymer containing 1,2,4-benzotriazine oxides.

1,2,4-Benzotriazine oxides are known compounds. U.S. Pat. No. 3,980,779 discloses 3-amino-1,2,4-benzotriazine-1,4-di-oxide compositions having the formula

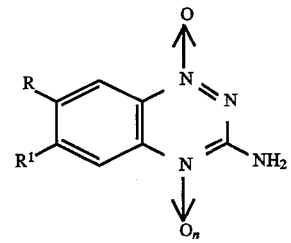

wherein
one of R and $R^1$ is hydrogen, halogen, lower alkyl, halo (lower alkyl), lower alkoxy, carbamoyl, sulfonamido, carboxy or carbo (lower alkoxy) and the other of R and $R^1$ is halogeno, lower alkyl, halo (lower alkyl), lower alkoxy, carbamoyl, sulfonamido, carboxy or carbo (lower alkoxy),
as antimicrobial composition used to promote livestock growth.

U.S. Pat. No. 5,175,287 issued Dec. 29, 1992 discloses the use of 1,2,4-benzotriazine oxides in conjunction with radiation for treatment of tumors. The 1,2,4-benzotriazine oxides sensitize the tumor cells to radiation and make them more amenable to this treatment modality.

Holden et al (1992) "Enhancement of Alkylating Agent Activity by SR-4233 in the FSaIIC Murine Fibrosarcoma" JNCI 84: 187–193 discloses the use of SR-4233, namely 3-amino-1,2,4-benzotriazine-1,4-dioxide, also known and hereinafter sometimes referred to as tirapazamine, in combination with an antitumor alkylating agent. The four antitumor alkylating agents, cisplatin, cyclophosphamide, carmustine and melphalan, were each tested to examine the ability of tirapazamine to overcome the resistance of hypoxic tumor cells to antitumor alkylating agents. Tirapazamine was tested alone and in combination with varying amounts of each of the antitumor alkylating agents. When SR-4233 was administered just before single-dose treatment with cyclophosphamide, carmustine or melphalan marked dose enhancement leading to synergistic cytotoxic effects on tumor cells was observed.

International Application No. PCT/US89/01037 discloses 1,2,4-benzotriazine oxides as radiosensitizers and selective cytotoxic agents. Other related patents include: U.S. Pat.

Nos. 3,868,372 and 4,001,410 which disclose the preparation of 1,2,4-benzotriazine oxides; and U.S. Pat. Nos. 3,991,189 and 3,957,799 which disclose derivatives of 1,2,4-benzotriazine oxides.

SUMMARY OF THE INVENTION

The present invention provides an implant formulation comprising: a biodegradable, slow release polymer as vehicle admixed with a compound of the formula (I)

I The present invention provides a capsule formulation comprising: a fractionated coconut oil formulation or a soybean oil formulation as vehicles admixed with a compound of the formula (I)

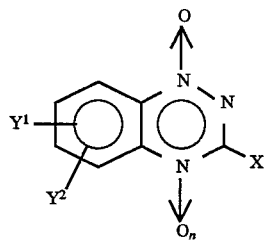

wherein X is H; hydrocarbyl (1-4C); hydrocarbyl (1-4C) substituted with OH, $NH_2$, NHR or NRR; halogen; OH; alkoxy (1-4C); $NH_2$; NHR or NRR; wherein each R is independently selected from lower alkyl (1-4C) and lower acyl (1-4C) and lower alkyl (1-4C) and lower acyl (1-4C) substituted with OH, $NH_2$, alkyl (1-4C) secondary and dialkyl (1-4C) tertiary amino groups, alkoxy (1-4C) or halogen; and when X is NRR, both R's taken together directly or through a bridge oxygen to form a morpholino ring, pyrrolidino ring or piperidino ring;

n is 0 or 1; and $Y^1$ and $Y^2$ are independently either H; nitro; halogen; hydrocarbyl (1-14C) including cyclic and unsaturated hydrocarbyl, optionally substituted with 1 or 2 substituents selected from the group consisting of halogen, hydroxy, epoxy, alkoxy (1-4C), alkylthio (1-4C), primary amino ($NH_2$), alkyl (1-4C) secondary amino, dialkyl (1-4C) tertiary amino, dialkyl (1-4C) tertiary amino where the two alkyls are linked together to produce a morpholino, pyrrolidino or piperidino, acyloxy (1-4C), acylamido (1-4C) and thio analogs thereof, acetylaminoalkyl (1-4C), carboxy, alkoxycarbonyl (1-4C), carbamyl, alkylcarbamyl (1-4C), alkylsulfonyl (1-4C) or alkylphosphonyl (1-4C), wherein the hydrocarbyl can optionally be interrupted by a single ether (—O—) linkage; or wherein $Y^1$ and $Y^2$ are independently either morpholino, pyrrolidino, piperidino, $NH_2$, NHR', NR'R'O(CO)R', NH(CO)R', O(SO)R', or O(POR')R' in which R' is a hydrocarbyl (1-4C) which may be substituted with OH, $NH_2$, alkyl (1-4C) secondary amino, dialkyl (1-4C) tertiary amino, morpholino, pyrrolidino, piperidino, alkoxy (1-4C), or halogen substituents, or pharmacologically acceptable salt of said compound.

The preferred compound used in the present invention is 3-amino-1,2,4-benzotriazine (tirapazamine).

The present invention is also directed to a method of cancer tumor treatment comprising: implanting into the site of the tumor in need of such treatment a biodegradable, slow release polymer containing an effective amount of a compound of formula (I) as defined herein.

As used herein, susceptibility of a tumor to an agent refers to an agent that is capable of exerting a therapeutic effect on a tumor by any mechanism such as by killing tumor cells, reducing cell proliferation, inhibiting sublethal damage repair or reducing the size of the tumor. Also as used herein, effective amount of the compound of Formula I as defined herein, refers to amounts capable of killing tumor cells or capable of killing tumor cell in conjunction with a radiation agent. An effective amount of a chemotherapy agent refers to an amount of the chemotherapy agent capable of killing cancer cells or otherwise producing a therapeutic effect such as by reducing tumor size or slowing tumor cell growth and proliferation. The percentage of active component in the composition and method for treating cancer tumors can be varied so that a suitable dosage is obtained. The dosage implanted into a particular patient is variable depending upon the clinician's judgment using as the criteria: the size of the tumor, the duration of treatment, the size and condition of the patient, the potency of the active component, and the patient's response thereto. An effective dosage amount of active component can thus readily be determined by the clinician considering all criteria and utilizing his best judgment on the patient's behalf.

We have found that the method of the present invention achieves the best results when the implanted disk is used in conjunction with systemically injected tirapazamine and the cancer tumor is subjected to radiation.

The composition of the implantable disc may contain, based on the total weight of the disk, of from about 0.1 to about 50%, and preferably of from about 1 to 25% w/w of tirapazamine. The size of disc may be of from about 0.5 to about 5 mm or larger and preferably of from about 1 to about 3 mm in diameter, and of from about 0.5 to about 2 mm in height. The desired rate of release may be obtained by varying the extent of polymerization of the biodegradable polymer as well known by those skilled in the art.

DETAILED DESCRIPTION OF THE INVENTION

Hypoxic cells make up a significant proportion of solid tumor cell populations and are implicated in the relative unresponsiveness of some human malignancies to current therapeutic modalities. The presence of these hypoxic cells in human tumors may make the tumors resistant to chemotherapy and radiotherapy as shown by Hockel, M; et at. Tumor oxygenation: A new predictive parameter in locally advanced cancer of the uterine cervix. Gyn. Onc. 51: 141–149;(1993); Kim, I. H; et at. Reoxygenation and rehypoxiation in the SCCVII mouse tumor. Int. J. Radiat. Oncol. Biol. Phys. 29: 493–497;(1994); Overgaard, J; et at. Nimorazole as a hypoxic radiosensitizer in treatment of supraglottic larynx and pharyngeal carcinoma. First report from the Danish Head and Neck Cancer Study (DAHANCA) protocol 5–85. Radiother. and Oncol. Suppl. 20: 143–149;(1991); Kornblith, P. L.; et al. Chemotherapy for malignant gliomas. J. Neurosurg. 68: 1–17;(1988); Lee, D. J.; et at. Logistics in designing clinical trials for etanidazole (SR 2508): an RTOG experience. Int. J. Radial. Oncol. Biol. Phys. 22: 569–571; (1992); and Mayer, R.; et al. A new method for determining dose rate distribution from radioimmunotherapy using radiochromic medium. Int. J. Radiat. Oncol. Biol. Phy. 28: 505–513;(1993). An estimated 12 to 20% of human tumor cells are hypoxic, while some cells cycle between aerobic and hypoxic states, as reported by: Dorie, M. J.; et al. Comparison of the enhancement of tumor responses to fractionated irradiation by SR 4233 (Tirapazamine) and by nicotinamide with carbogen. Int. J. Radiat. Onocol. Biol. Phys. 28: 145–150;(1993).

It has been shown that hypoxic cells require two or three times more radiation to produce the same level of ceil killing as do normally oxygenated cells: Phillips, T.; et al. Clinical trials of hypoxic cell sensitizers. Int. J. Radiat. Oncol. Biol. Phys. 8: 327-334;(1982).

Furthermore, the ability of radiation to cure some tumors has been attributed to reoxygenation of hypoxic tumor cells occurring during fractionated radiotherapy: Salazar, O. M; et at. High dose radiation therapy in the treatment of malignant gliomas: final report. Int. J. Radiat. Onocol. Biol. Phys. 3: 1733-1740;(1979). Consequently, immediately after tumor irradiation, the hypoxic function rises and can reach nearly 100% of the surviving cells due to surviving cells due to the preferential inactivation of radiosensitive aerobic cells. In some studies the time interval of reoxygenation has been reported to be between 2 to 6 hours; therefore, a therapeutic agent which kills hypoxic radioresistant tumor cells may increase the effectiveness of radiotherapy as a treatment of cancers including high grade brain gliomas.

The factors that limit the effectiveness of hypoxic cell sensitizers include inherently small enhancement ratios, limited dosing due to systemic toxicities, the fact that not all tumors contain hypoxic regions, and that tumor cells reoxygenate during fractionated radiotherapy. As an example, nitroimidazol hypoxic cell sensitizers have been studied in clinical trials for the last 20 years, and with few exceptions, the results are either negative or inconclusive.

Tirapazamine, the preferred member of the 1, 2, 4-benzotriazine oxide family of compounds used in the present invention, is a bioreductive agent which, by undergoing a one-electon reduction in a hypoxic environment, forms cytotoxic free radicals that cause DNA strand breaks and cell death as reported by: Brown, J. M. SR 4233 (Tirapazamine): a new anticancer drug exploiting hypoxia in solid tumors. B R. J. Cancer. 67: 1163-1170;(1993).

In our studies reported here, IP injected tirapazamine alone had no effect on the mean VDT, but had significant effect when combined with radiation. The lengthening of mean VDT was increased from 12 days for fractionated radiation (2 Gy×6) to 25 days for fractionated radiation plus the drug. However, tirapazamine alone in our experimental schedule. did not alter the mean VDT significantly, suggesting that the drug must interact with fractionated radiation.

Other studies using mouse squamous cell VII tumors have demonstrated that within one hour of injecting tirapazamine, the hypoxic fraction fell to 0.57% (about 7% of pretreatment levels) and returns to pretreatment levels 3 to 5 hours later. This rehypoxiation phenomenon helped us to realize that tirapazamine should be delivered at the site of the tumor and be present in a slow release form to maintain hypoxiation of the tumor cells. Hence, it was discovered that intratumoral implantation of a tirapazamine containing polymer in a suitable form, such as a disc, has the advantage of maintaining a local anti-tumor effect while avoiding systemic toxicities. Optimal tumor response was seen when local and systemic tirapazamine were combined; perhaps due to differential targeting within the tumor xenograft.

The description of clinical studies follows.

MATERIALS AND METHODS

Tumor Cell line: The human GBM cell line (U251) used in the study was obtained from the DCT Tumor Repository, National Cancer Institute. Cells were cultured in Delbecco's MEM/Ham's F-12 nutrient mixture with 10% fetal bovine serum (GIBCO) and antibodies (penicillin and streptomycin) in 12×80 mm plastic culture dishes or T25 culture flasks. Cells were incubated (37° C.) in a mixture of 5% carbon dioxide and 95% air. Media were changed twice weekly and cells were passaged at confluence with 0.5% trypsin.

Nude mouse xenonaft: Six week old male Balb/c athymic nude mice received subcutaneous injections of $4\times10^6$ (experiment A) and $5\times10^6$ (experiment B) U251 cells in the left posterior extremity. Tumors were visible after 6 to 8 days. Tumor sizes ranged from 0.51–1.2 cm$^3$ at the start of the treatment. Mice were assigned to treatment groups so that each group had a mean tumor volume of approximately 0.8 cm$^3$. Mice were sacrificed after tumors reached at least twice their original tumor volume.

Systemic Administration of Tirapazamine: The drug was supplied by Sanoff Winthrop, Collegeville, Pa. Tirapazamine was dissolved in physiological saline at a concentration of 0.71 mg/ml and intraperitoneal (IP) injections were given in a volume of 0.02 ml/g body weight (0.08 mmole/kg). Animals in experiment A received daily injections, and animals in experiment B received injections twice daily over 3 consecutive days for a total of 6 injections.

Polymer Synthesis; Carboxyphenoxypropane monomer and prepolymer, sebacic acid (SA) prepolymer, and poly(bis (p-carboxyphenoxy)-propane (PCPP):SA) polymer were prepared by a melt polycondensation process (PCPP:SA ratio=20:80). The prepolymers were refluxed with acetic acid anhydride, recrystalized from dry toluene, immersed in dry petroleum ether to extract acetic acid and toluene, and placed under high vacuum to allow polymerization. The acetic anhydride produced by the polymerization process was removed by vacuum. The polymer was allowed to solidify at room temperature and then was dissolved in methylene chloride with petroleum ether and hexane. The precipitate was washed three times with diethyl ether to remove residual acetic anhydride and was then dried under vacuum.

The synthesis is described in detail by: Chasin, M.; et al. Polyanhydrides for controlled drug delivery. Biopharm. Manufact. 1: 33–46;(1988); and Domb, A.; et al. Polyanhydrides. I. Preparation of high molecular weight polyanhydrides. J. Exp. Med. 112: 509–531; (1987).

Tirapazamine Polymer Formulation: 2 mg tirapazamine and 8 mg PCPP:SA polymer were combined in methylene chloride (10% wt/wt). The solvents were removed by desiccation under vacuum. The tirapazamine containing polymers were then pressed into discs measuring 3 mm in diameter and 1 mm in height. Each disc weighed 10 mg.

Release Kinetics in Vitro: Tirapazamine polymer discs were incubated for known intervals in 1 ml of 0.1M phosphate-buffered saline (PBS) at 30° C. The PBS was periodically removed, replaced with fresh saline. Tirapazamine levels were measured using spectophotometry (Beckman model DU-65, Beckman Instruments, Fullerton, Calif.) at a wavelength of 515 nanometers. The percentage of loaded tirapazamine that accumulated in the supernatant was plotted vs. time. The rate of release after one day was 8% and after 3 days was 11% with a continuing steady rate of release thereafter. After 16 days the rate of release was about 18%.

Implantation of Polymer Discs:. For surgical implantation of polymer discs, animals were anesthetized with methoxyflurane, a skin incision was made next to the xenograft, and an empty disc or tirapazamine disc was inserted in the center of the tumor via a single 3–4 mm incision. The incision was closed using wound clips. Contralateral flank polymer discs were placed subcutaneously using the same technique.

In Vivo Irradiation: A Mark I Irradiator (Model 68, J. L. Shepherd and Assoc.) was used for in vivo irradiation. The dose to the xenograft was calibrated using TLD dosimetry and confirmed with radiochromic dye media (Gafchromic) mouthed in polystyrene mouse phantoms. The tumor bearing flank was selectively irradiated, with shielding of the mouse trunk and head. In experiment A, irradiation began on the first day of IP tirapazamine injection, and animals received 2 Gy×6 consecutive daily fractions. In experiment B, irradiation and systemic tirapazamine administration began one day following polymer disc implantation and animals received 2 Gy twice daily (separated by 5–6 hours) over 3 consecutive days for a total of 6 fractions. Radiation treatments were given 5–20 minutes following IP drag or saline injections.

Tumor Volumetrics: Tumor length (L), width (W), and height (H) were measured twice weekly and tumor volumes were calculated as pi/6×L×W×H. The logarithm of the ratio of this product (V) to the initial product (VO) for each animal was calculated and the mean logarithm of this ratio for each treatment group was plotted versus time. The time of regrowth to twice the original tumor volume (V/VO=2; log V/VO=0.3) for each animal and treatment group was calculated from the plot of log V/VO vs. time. Mean tumor volume doubling time (VDT) was used as the endpoint to determine efficacy of a given treatment arm on U251 xenograft tumors. Each animal was weighed bi-weekly to assess possible toxicity to treatment.

Statistical Evaluation: Data show the mean±standard error of the mean (SEM). Outcomes among experimental groups were compared using the two tailed Student's test.

RESULTS

Systemic delivery Of Tirapazamine: Experiment A was performed to test the efficacy of tirapazamine alone or combined with daily irradiation on the U251 GBM xenograft. As shown in Table 1, drug alone had no effect on mean volume doubling time (VDT). Xenografts receiving saline (control) or daily tirapazamine alone had a mean VDT of 10 and 12 day respectively (p=0.6). Fractionated radiation plus saline injections produced a significant growth delay (VDT=22 days, P=0.012) and this radiation effect was further enhanced with the addition of IP injections of tirapazamine (VDT=35 days, P=0.012).

TABLE 1

Experiment A: U251 xenograft response to systemic delivery of tirazapamine

| Group | Number of Animals | Radiation, 2Gy (daily × 6) | IP Tirapazamine (daily × 6) | VDT* (days) |
|---|---|---|---|---|
| 1 | 3 | No | No | 10 ± 0 |
| 2 | 4 | No | Yes | 12 ± 0.6 |
| 3 | 5 | Yes | No | 22 ± 2.5 |
| 4 | 5 | Yes | Yes | 35 ± 2.5 |

*Mean xenograft tumor volume doubling time ± SEM

Student's t test: Effect of radiation: group 1 vs 3, P = 0.012; 2 vs 4, P < 0.001. Effect of IP tirapazamine group 1 vs. 2, P = 0.6; 3 vs 4, P = 0.012.

Intralesional delivery of tirapazamine by polymer implants: After establishing the antitumor effect of systemic administration of tirapazamine on GBM xenografts, experiment B was done to evaluate intralesional polymer delivery of tirapazamine alone or combined with irradiation. Radiation and/or IP treatments began one day following implantation of the polymer discs, with the radiation given twice per day to possibly take advantage of the initial steep slope of the tirapazamine release curve. In order to distinguish a systemic effect of drug released from the drug implant from a true local phenomenon, multiple groups were used, including a group with drug implants placed in the opposite flank. Table 2 and FIG. 3 show the assigned treatment groups, mean VDT of each group and values for various comparisons.

TABLE 2

Experiment B: U251 xenograft response to systemic and intratumoral polymer delivery of tirapazamine

| Group | Number of Animals | Radiation, 2Gy (bid × 3 days) | Polymer implant | IP Tirapazamine (bid × days) | VDT* |
|---|---|---|---|---|---|
| 1 | 4 | No | tumor, empty | No | 7 ± 1.96 |
| 2 | 4 | No | tumor, drug | Yes | 10.5 ± .87 |
| 3 | 4 | Yes | tumor, empty | No | 19.3 ± .76 |
| 4 | 5 | Yes | contralateral flank drug and tumor, empty | No | 16.4 ± 1.57 |
| 5 | 5 | Yes | tumor, drug | No | 23.0 ± 2.49 |
| 6 | 5 | Yes | tumor, empty | Yes | 24.8 ± 3.0 |
| 7 | 5 | Yes | tumor, drug | Yes | 35.8 ± 2.0 |

*Mean xenogaft tumor doubling time ± SEM + site if implant, loading (drug = tirapazamine)
Student's t test: Effect of radiation: group 1 vs 3, P = 0.001; 2 vs 7, P < 0.001. Effect of IP tirapazamine: group 3 vs 6, P = 0.15; 5 vs 7, P = 0.004. Effect of tira-wafer: group 3 vs 5, P = 0.24; 6 vs 7, P = 0.016; 4 vs 5, P = 0.055. Effect of IP tirapazamine + tira-wafer: group 1 vs 2, P = 0.15; 3 vs 7, P < 0.001.

The combination of tumor drug implant plus IP tirapazamine added to radiation (group 7) produced a large growth delay (16.5 days, P<0.001) as compared to radiation alone controls. This was much larger than the delay of tumor drug implant plus IP tirapazamine (3.5 days, P=0.15) compared to tumor empty polymer implant. (group 1). Group 7 also had a significant growth delay when compared to IP tirapazamine alone plus radiation (11.8 days, P=0.016) or tumor drug implant alone plus radiation (12.8 days, P=0.004). Thus, both the tirapazamine polymer implant and IP tirapazamine appear to be contributing to the effectiveness of the combination with radiation.

Delays produced by tumor drug implant alone or IP tirapazamine alone added to radiation did not reach significance. The delay for tumor drug implant plus radiation (group 5) compared to tumor empty polymer implant plus radiation (group) was 3.7 days (P=0.24) and compared to tumor empty polymer implant plus contralateral drug implant with radiation was 6.6 days (P=0.055). For tumor empty polymer implant plus IP tirapazamine with radiation (group 6) compared to tumor empty polymer implant plus radiation the delay was 5.5 days (P=0.15).

Toxicity: Table 3 shows the mean low and final animal weights as a fraction of the pretreatment weight for each group in experiment B. Transient weight loss was seen in all treatment groups as compared to group 1, which only received a blank tumor implant. The results indicate that radiation or the combination of IP and polymer tirapazamine produced systemic toxicity and that for the latter, toxicity appeared to be primarily associated with the IP treatments. The weight losses were transient, with all groups exceeding their pretreatment weights prior to sacrifice.

TABLE 3

Mean low and final animal weights (± SEM)

| Group | Low weight post treatment/ Pretreatment weight | Final body weight/ Pretreatment weight |
|---|---|---|
| 1 | 1.01 ± .02 | 1.10 ± .02 |
| 2 | 0.95 ± .01 | 1.05 ± .04 |
| 3 | 0.94 ± .02 | 1.10 ± .03 |
| 4 | 0.96 ± .02 | 1.08 ± .02 |
| 5 | 0.95 ± .01 | 1.06 ± .01 |
| 6 | 0.89 ± .01 | 1.09 ± .03 |
| 7 | 0.85 ± .03 | 1.06 ± .03 |

Students t test: Effect of radiation: group 1 vs 3, P=0.044, 2 vs 7, P=0.033. Effect of IP tirapazamine: 3 vs 6, P=0.059, 5 vs 7, P=0.006. Effect of tira-wafer: group 3 vs 4, P=0.43; 3 vs 5, P=0.64, 6 vs 7, P=0.19. Effect of IP tirapazamine+ tira-wafer: group 1 vs 2, P=0.033; 3 vs 7, P=-0.029.

Clinical studies thus indicate that it is of great advantage to deliver tirapazamine intralesionally in order to avoid systemic toxicity, maximize exposure directly to the tumor and target hypoxic regions. The implants made of biodegradable polymers allow sustained controlled release of the drug and provide a superior alternative; or adjunct, to systemic administration. The advantages of the implants include predictable biodegradation, continuous release of the drug, and absorption by the body after implantation, rendering removal unnecessary.

Having described the invention with reference to its preferred embodiments, it is to be understood that modification's within the scope of the invention will be apparent to those skilled in the art.

What is claimed is:

1. A solid, sustained and controlled release implantable formulation for the treatment of cancer tumors comprising based on the total weight of the formulation: of from about 0.1 to about 50% of an anticancer tumor compound of the formula (I)

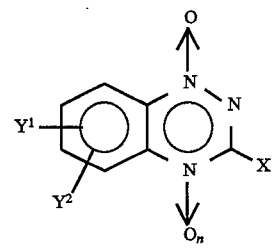

wherein X is H; hydrocarbyl (1-4C); hydrocarbyl (1-4C) substituted with OH, $NH_2$, NHR or NRR; halogen; OH; alkoxy (1-4C); $NH_2$; NHR or NRR; wherein each R is independently selected from lower alkyl (1-4C) and lower acyl (1-4C) and lower alkyl (1-4C) and lower acyl (1-4C) substituted with OH, $NH_2$, alkyl (1-4C) secondary and dialkyl (1-4C) tertiary amino groups, alkoxy (1-4C) or halogen; and when X is NRR, both R's taken together directly or through a bridge oxygen to form a morpholino ring, pyrrolidino ring or piperidino ring;

n is 0 or 1; and $Y^1$ and $Y^2$ are independently either H; nitro; halogen; hydrocarbyl (1-14C) including cyclic and unsaturated hydrocarbyl, optionally substituted with 1 or 2 substituents selected from the group consisting of halogen, hydroxy, epoxy, alkoxy (1-4C), alkylthio (1-4C), primary amino ($NH_2$), alkyl (1-4C) secondary amino, dialkyl (1-4C) tertiary amino, dialkyl (1-4C) tertiary amino where the two alkyls are linked together to produce a morpholino, pyrrolidino or piperidino, acyloxy (1-4C), acylamido (1-4C) and thio analogs thereof, acetylaminoalkyl (1-4C), carboxy, alkoxycarbonyl (1-4C), carbamyl, alkylcarbamyl (1-4C), alkylsulfonyl (1-4C) or alkylphosphonyl (1-4C), wherein the hydrocarbyl can optionally be interrupted by a single ether (—O—) linkage; or wherein $Y^1$ and $Y^2$ are independently either morpholino, pyrrolidino, piperidino, $NH_2$, NHR', NR'R'O(CO)R', NH(CO)R', O(SO)R', or O(POR')R' in which R' is a hydrocarbyl (1-4C) which may be substituted with OH, $NH_2$, alkyl (1-4C) secondary amino, dialkyl (1-4C) tertiary amino, morpholino, pyrrolidino, piperidino, alkoxy (1-4C), or halogen substituents, or pharmacologically acceptable salt of said compound contained in a solid, biodegradable polymer disc capable of sustained and controlled releasing of said compound.

2. The solid, sustained and controlled release, implantable formulation of claim 1 wherein said anti cancer tumor compound is 3-amino 1, 2, 4-benzotriazine.

3. The solid, sustained and controlled release, implantable formulation of claim 1 wherein said anti cancer tumor compound is present in said formulation in an amount of from about 1 to about 25% w/w.

4. The solid, sustained and controlled release, implantable formulation of claim 1 wherein said solid, biodegradable polymer is a polyanhydride polymer.

5. The solid, sustained and controlled release, implantable formulation of claim 1 wherein said sustained and controlled release is of from about one hour to sixteen days.

6. The solid, sustained and controlled release, implantable formulation of claim 1 wherein said disc is of dimensions having of from about 0.5 to about 5 mm diameter; and of from about 0.5 to about 2 mm height.

7. A method of treating cancer tumors in a mammal comprising: administering to said mammal in need of such treatment by implantation an effective amount of the formulation of claim 1.

8. The method of claim 7 wherein said formulation contains 3-amino 1, 2, 4-benzotriazine.

9. A method of treating cancer tumors in a mammal comprising:

administering to said mammal in need of such treatments by implantation an effective amount of the solid, sustained and controlled release formulation of claim 1; and parenterally administering an effective amount of a compound the formula (I)

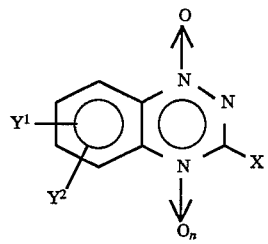

wherein X is H; hydrocarbyl (1-4C); hydrocarbyl (1-4C) substituted with OH, $NH_2$, NHR or NRR; halogen; OH; alkoxy (1-4C); $NH_2$; NHR or NRR; wherein each R is independently selected from lower alkyl (1-4C) and lower acyl (1-4C) and lower alkyl (1-4C) and lower acyl (1-4C) substituted with OH, $NH_2$, alkyl (1-4C) secondary and dialkyl (1-4C) tertiary amino groups, alkoxy (1-4C) or halogen; and when X is NRR, both R's taken together directly or through a bridge oxygen to form a morpholino ring, pyrrolidino ring or piperidino ring;

n is 0 or 1; and $Y^1$ and $Y^2$ are independently either H; nitro; halogen; hydrocarbyl (1-14C) including cyclic and unsaturated hydrocarbyl, optionally substituted with 1 or 2 substituents selected from the group consisting of halogen, hydroxy, epoxy, alkoxy (1-4C), alkylthio (1-4C), primary amino ($NH_2$), alkyl (1-4C) secondary amino, dialkyl (1-4C) tertiary amino, dialkyl (1-4C) tertiary amino where the two alkyls are linked together to produce a morpholino, pyrrolidino or piperidino, acyloxy (1-4C), acylamido (1-4C) and thio analogs thereof, acetylaminoalkyl (1-4C), carboxy, alkoxycarbonyl (1-4C), carbamyl, alkylcarbamyl (1-4C), alkylsulfonyl (1-4C) or alkylphosphonyl (1-4C), wherein the hydrocarbyl can optionally be interrupted by a single ether (—O—) linkage; or wherein $Y^1$ and $Y^2$ are independently either morpholino, pyrrolidino, piperidino, $NH_2$, NHR', NR'R'O(CO)R', NH(CO)R', O(SO)R', or O(POR')R' in which R' is a hydrocarbyl (1-4C) which may be substituted with OH, $NH_2$, alkyl (1-4C) secondary amino, dialkyl (1-4C) tertiary amino, morpholino, pyrrolidino, piperidino, alkoxy (1-4C), or halogen substituents, or pharmacologically acceptable salt of said compound contained in a pharmaceutically acceptable carrier.

10. The method of claim 9 wherein said compound in said formulation and in said formula (I) is 3-amino 1, 2, 4-benzotriamine.

11. The method of claim 9 wherein said formulation contains of from about 99.9 to about 50% w/w of a polyanhydride polymer.

12. A method of treating cancer tumors in a mammal comprising:

administering to said mammal in need of such treatments by implantation an effective amount of the solid, sustained and controlled release formulation of claim 1; and orally administering an effective amount of a compound of the formula (I)

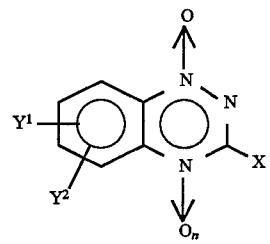

wherein X is H; hydrocarbyl (1-4C); hydrocarbyl (1-4C) substituted with OH, $NH_2$, NHR or NRR; halogen; OH; alkoxy (1-4C); $NH_2$; NHR or NRR; wherein each R is independently selected from lower alkyl (1-4C) and lower acyl (1-4C) and lower alkyl (1-4C) and lower acyl (1-4C) substituted with OH, $NH_2$, alkyl (1-4C) secondary and dialkyl (1-4C) tertiary amino groups, alkoxy (1-4C) or halogen; and when X is NRR, both R's taken together directly or through a bridge oxygen to form a morpholino ring, pyrrolidino ring or piperidino ring;

n is 0 or 1; and $Y^1$ and $Y^2$ are independently either H; nitro; halogen; hydrocarbyl (1-14C) including cyclic and unsaturated hydrocarbyl, optionally substituted with 1 or 2 substituents selected from the group consisting of halogen, hydroxy, epoxy, alkoxy (1-4C), alkylthio (1-4C), primary amino ($NH_2$), alkyl (1-4C) secondary amino, dialkyl (1-4C) tertiary amino, dialkyl (1-4C) tertiary amino where the two alkyls are linked together to produce a morpholino, pyrrolidino or piperidino, acyloxy (1-4C), acylamido (1-4C) and thio analogs thereof, acetylaminoalkyl (1-4C), carboxy, alkoxycarbonyl (1-4C), carbamyl, alkylcarbamyl (1-4C), alkylsulfonyl (1-4C) or alkylphosphonyl (1-4C), wherein the hydrocarbyl can optionally be interrupted by a single ether (—O—) linkage; or wherein $Y^1$ and $Y^2$ are independently either morpholino, pyrrolidino, piperidino, $NH_2$, NHR', NR'R'O(CO)R', NH(CO)R', O(SO)R', or O(POR')R' in which R' is a hydrocarbyl (1-4C) which may be substituted with OH, $NH_2$, alkyl (1-4C) secondary amino, dialkyl (1-4C) tertiary amino, morpholino, pyrrolidino, piperidino, alkoxy (1-4C), or halogen substituents, or pharmacologically acceptable salt of said compound contained in a pharmaceutically acceptable carrier.

13. The method of claim 12 wherein said compound in said formulation and in said formula (I) is 3-amino 1, 2, 4-benzotriazine.

14. The method of claim 12 wherein said formulation contains of from about 99.9 to about 50% w/w of a polyanhydride polymer.

15. A method of treating cancer tumors in a mammal comprising:

administering to said mammal in need of such treatments by implantation an effective amount of the solid, sustained and controlled release formulation of claim 1;

parenterally administering an effective amount of a compound of the formula (I)

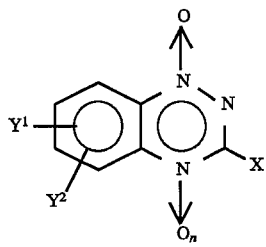

wherein X is H; hydrocarbyl (1-4C); hydrocarbyl (1-4C) substituted with OH, $NH_2$, NHR or NRR; halogen; OH; alkoxy (1-4C); $NH_2$; NHR or NRR; wherein each R is independently selected from lower alkyl (1-4C) and lower acyl (1-4C) and lower alkyl (1-4C) and lower acyl (1-4C) substituted with OH, $NH_2$, alkyl (1-4C) secondary and dialkyl (1-4C) tertiary amino groups, alkoxy (1-4C) or halogen; and when X is NRR, both R's taken together directly or through a bridge oxygen to form a morpholino ring, pyrrolidino ring or piperidino ting;

n is 0 or 1; and $Y^1$ and $Y^2$ are independently either H; nitro; halogen; hydrocarbyl (1-14C) including cyclic and unsaturated hydrocarbyl, optionally substituted with 1 or 2 substituents selected from the group consisting of halogen, hydroxy, epoxy, alkoxy (1-4C), alkylthio (1-4C), primary amino ($NH_2$), alkyl (1-4C) secondary amino, dialkyl (1-4C) tertiary amino, dialkyl (1-4C) tertiary amino where the two alkyls are linked together to produce a morpholino, pyrrolidino or piperidino, acyloxy (1-4C), acylamido (1-4C) and thio analogs thereof, acetylaminoalkyl (1-4C), carboxy, alkoxycarbonyl (1-4C), carbamyl, alkylcarbamyl (1-4C), alkylsulfonyl (1-4C) or alkylphosphonyl (1-4C), wherein the hydrocarbyl can optionally be interrupted by a single ether (—O—) linkage; or wherein $Y^1$ and $Y^2$ are independently either morpholino, pyrrolidino, piperidino, $NH_2$, NHR', NR'R'O(CO)R', NH(CO)R', O(SO)R', or O(POR')R' in which R' is a hydrocarbyl (1-4C) which may be substituted with OH, $NH_2$, alkyl (1-4C) secondary amino, dialkyl (1-4C) tertiary amino, morpholino, pyrrolidino, piperidino, alkoxy (1-4C), or halogen substituents, or pharmacologically acceptable salt of said compound contained in a pharmaceutically acceptable carrier; and subjecting said cancer tumor to radiation treatment.

16. The method of claim 15 wherein said compound in said formulation and in said formula (I) is 3-amino 1, 2, 4-benzotriazine.

17. The method of claim 15 wherein said formulation contains of from about 99.9 to about 50% w/w of a polyanhydride polymer.

18. A method of treating cancer tumors in a mammal comprising:

administering to said mammal in need of such treatment by implantation an effective amount of the solid, sustained and controlled release formulation of claim 1;

orally administering an effective amount of a compound of the formula (I)

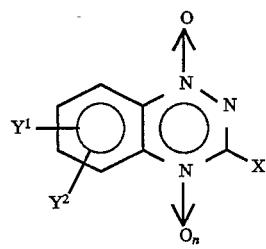

wherein X is H; hydrocarbyl (1-4C); hydrocarbyl (1-4C) substituted with OH, $NH_2$, NHR or NRR; halogen; OH; alkoxy (1-4C); $NH_2$; NHR or NRR; wherein each R is independently selected from lower alkyl (1-4C) and lower acyl (1-4C) and lower alkyl (1-4C) and lower acyl (1-4C) substituted with OH, $NH_2$, alkyl (1-4C) secondary and dialkyl (1-4C) tertiary amino groups, alkoxy (1-4C) or halogen; and when X is NRR, both R's taken together directly or through a bridge oxygen to form a morpholino ring, pyrrolidino ring or piperidino ring;

n is 0 or 1; and $Y^1$ and $Y^2$ are independently either H; nitro; halogen; hydrocarbyl (1-14C) including cyclic and unsaturated hydrocarbyl, optionally substituted with 1 or 2 substituents selected from the group consisting of halogen, hydroxy, epoxy, alkoxy (1-4C), alkylthio (1-4C), primary amino ($NH_2$), alkyl (1-4C) secondary amino, dialkyl (1-4C) tertiary amino, dialkyl (1-4C) tertiary amino where the two alkyls are linked together to produce a morpholino, pyrrolidino or piperidino, acyloxy (1-4C), acylamido (1-4C) and thio analogs thereof, acetylaminoalkyl (1-4C), carboxy, alkoxycarbonyl (1-4C), carbamyl, alkylcarbamyl (1-4C), alkylsulfonyl (1-4C) or alkylphosphonyl (1-4C), wherein the hydrocarbyl can optionally be interrupted by a single ether (—O—) linkage; or wherein $Y^1$ and $Y^2$ are independently either morpholino, pyrrolidino, piperidino, $NH_2$, NHR', NR'R'O(CO)R', NH(CO)R', O(SO)R', or O(POR')R' in which R' is a hydrocarbyl (1-4C) which may be substituted with OH, $NH_2$, alkyl (1-4C) secondary amino, dialkyl (1-4C) tertiary amino, morpholino, pyrrolidino, piperidino, alkoxy (1-4C), or halogen substituents, or pharmacologically acceptable salt of said compound contained in a pharmaceutically acceptable carrier; and subjecting said cancer tumor to radiation treatment.

19. The method of claim 18 wherein said compound in said formulation and in said formula (I) is 3-amino 1,2,4-benzotriazine.

20. The method of claim 18 wherein said formulation contains from about 99.9 to about 50% w/w of a polyanhydride polymer.

* * * * *